United States Patent [19]
Baltruschat

[11] Patent Number: 5,977,026
[45] Date of Patent: Nov. 2, 1999

[54] HERBICIDAL MIXTURES

[75] Inventor: Helmut Siegfried Baltruschat, Schweppenhausen, Germany

[73] Assignee: American Cyanamid, Madison, N.J.

[21] Appl. No.: 08/902,650

[22] Filed: Jul. 30, 1997

Related U.S. Application Data

[60] Provisional application No. 60/023,062, Jul. 30, 1996.
[51] Int. Cl.⁶ .......................... A01N 33/00; A01N 43/40; A01N 43/54; A01N 43/64
[52] U.S. Cl. .......................... 504/130; 504/133; 504/134; 504/136; 504/137; 504/148
[58] Field of Search .................................. 504/130, 148, 504/133, 134, 136, 137

[56] References Cited

U.S. PATENT DOCUMENTS

| | | | |
|---|---|---|---|
| 5,242,892 | 9/1993 | Rebeiz | 504/129 |
| 5,453,414 | 9/1995 | Tice et al. | 504/133 |

FOREIGN PATENT DOCUMENTS

| | | |
|---|---|---|
| 0 572 093 | 12/1993 | European Pat. Off. . |
| WO 94/22833 | 10/1994 | WIPO . |
| WO 94/07368 | 4/1996 | WIPO . |

OTHER PUBLICATIONS

Chemical Abstracts, vol. 21 No. 9, Aug. 29, 1994.

*Primary Examiner*—Allen J. Robinson
*Attorney, Agent, or Firm*—Joseph M. Mazzarese

[57] ABSTRACT

A herbicidal composition containing
(1) a substituted pyridine of general formulae I or II

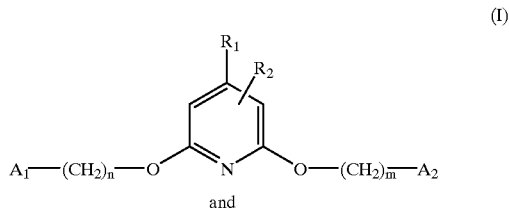

and

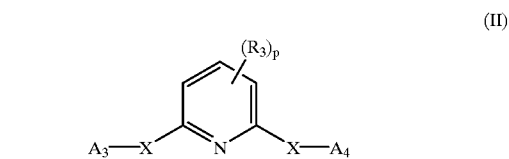

as defined herein,
and
(2) at least one herbicidal component selected from
a) an urea-type herbicide, such as chlortoluron, isoproturon, linuron or neburon,
b) a triazine-type herbicide, such as atrazine, cyanazine or simazine
c) a hydroxybenzonitrile herbicide, such as bromoxynil or ioxynil,
d) an aryloxyalkanoic acid herbicide, such as dichlorprop, MCPA or mecoprop,
e) a dinitroaniline herbicide, such as pendimethalin,
f) a sulfonylurea herbicide, such as amidosulfuron,
g) a pyridazine herbicide, such as pyridate,
h) a fluorene carboxylic acid herbicide, such as flurenol,
i) a pyridyloxyacetic acid herbicide, such as fluroxypyr,
j) a fenoxyfenoxypropion acid herbicide, such as fenoxaprop, and
k) an oxyacetamide herbicide,
which provides a synergistic effect against a broad spectrum of weed species, e.g., in cereal crops. The invention also provides a method for controlling weeds by applying both a compound (1) and a compound (2) to a locus.

12 Claims, No Drawings

HERBICIDAL MIXTURES

This application claims the benefit of U.S. Provisional Application Ser. No. 60/023,062, filed Jul. 30, 1996.

BACKGROUND OF THE INVENTION

The present invention relates to an improvement in the efficacy of herbicidal 2,6-substituted pyridines by combination with a selected second herbicidal compound. The term "2,6-substituted pyridines" is being used herein for such pyridine derivatives which may or may not contain further substituents.

The herbicidal 2,6-disubstituted pyridines to be used according to the present invention are a group of compounds, disclosed in European Patent Applications EP 0 572 093 A, EP 0 692 474 A, EP 0 693 490 and International Application WO 94/22833, which display excellent herbicidal performance, in particular against broad-leaved weeds in cereal crops. However, the 2,6-disubstituted pyridines, when used as the sole active ingredient, do not always achieve effective control of the full spectrum of weed species encountered in commercial agronomic applications, in conjunction with reliable selectivity for the crop species. Such gaps in the spectrum of control can be overcome by co-treatment with another herbicide known to be effective against the relevant weed species. The combined use of certain herbicidal pyridines and in addition other herbicides has been described in International Patent Application WO 94/07368.

Surprisingly, it has now been found, that the combined herbicidal activity of compounds from the above mentioned 2,6-disubstituted pyridines with various partners against many broad-leaved weeds and annual grasses is much greater than expected when applied pre- or post-emergence and that this activity cannot be ascribed to an additive effect, but to a remarkable degree of synergism on many broad-leaved weed species and annual grasses, for example on *Setaria viridis, Alopecurus myosuroides, Poa annua, Stellaria media, Lamium purpureum, Galium aparine, Veronica hederaefolia, Papaver rhoeas* or *Matricaria inodora* (i.e. these combinations show a much higher level of activity than predicted from that of the individual compounds) which enables also a greater selectivity for the crop species.

A mixture of herbicides shows synergistic effect if the herbicidal activity of the mixture is larger than the sum of activities of the seperately applied compounds. The expected herbicidal activity for a given mixture of two herbicides can be calculated as follows (See Colby, S. R., "Calculating synergistic and antagonistic response of herbicide combinations", Weeds 15, pp 20–22 (1967):

$$WE = X + \frac{Y \times (110 - X)}{100}$$

wherein

X is the percentage of growth inhibition upon treatment with a herbicide 1 at a dose of p kg/ha compared with an untreated control (X=0%)

Y is the percentage of growth inhibition treatment with a herbicide 2 at a dose of q kg/ha compared with an untreated control WE is the herbicidal effect to be expected upon treatment (% of growth inhibition compared with untreated control) with a combination of herbicide 1 and 2 at a dose of p+q g/ha, respectively.

If the actual weed control (W) exceeds the expected (calculated) weed control (WE), the mixture displays a synergistic effect.

SUMMARY OF THE INVENTION

The present invention incudes a herbicidal composition comprising a herbicidally acceptable carrier and/or surface active agent together with, as active ingredient, a mixture of:
(1) at least one herbicidal component selected from
  a) urea-type herbicide, such as chlortoluron, isoproturon, linuron or neburon,
  b) a triazine-type herbicide, such as atrazine, cyanazine or simazine,
  c) a hydroxybenzonitrile herbicide, such as bromoxynil or ioxynil,
  d) an aryloxyalkanoic acid herbicide, such as dichlorprop, 4-chloro-2-methylphenoxyacetic acid ("MCPA") or mecoprop,
  e) a dinitroaniline herbicide, such as pendimethalin,
  f) a sulfonylurea herbicide, such as amidosulfuron,
  g) a pyridazine herbicide, such as pyridate,
  h) a fluorene carboxylic acid herbicide, such as flurenol,
  i) a pyridyloxyacetic acid herbicide, such as fluroxypyr,
  j) a fenoxyfenoxypropionie acid herbicide, such as fenoxaprop, and
  k) an oxyacetamide herbicide, and
(2) at least one compound selected from the compounds of general formulae I and II

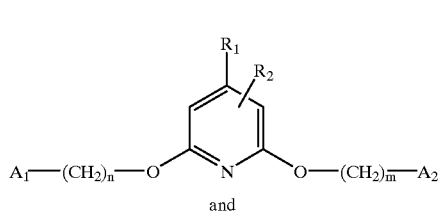

and

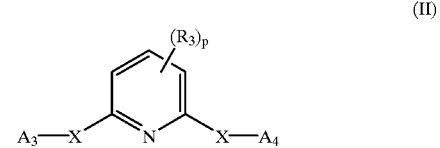

wherein
$A_1$ and $A_2$ independently represent an aryl group, at least one of $A_1$ and $A_2$ being substituted by one or more of the same or different substituents selected from halogen atoms, alkyl groups, alkoxy groups, haloalkyl groups and haloalkoxy groups;
$R_1$ represents a hydrogen atom, or a cyano group, or an alkyl, alkoxy, alkylthio or haloalkyl group having from 1 to 4 carbon atoms, and
$R_2$ represents a hydrogen or halogen atom, provided that at least one of $R_1$ and $R_2$ represents a hydrogen atom;
n and m independently represent 0 or 1;
$A_3$ represents an optionally substituted 5 or 6 membered nitrogen containing heteroaromatic group;
$A_4$ represents an optionally substituted 5 or 6 membered cyclic hydrocarbon, alkyl, alkenyl, alkynyl, aryl or aralkyl group or independently one of the meanings for $A_3$;
$R_3$ represents a halogen atom or an alkyl, haloalkyl, alkoxy, alkylthio or dialkylamino group;
X represents an oxygen or sulfur atom;
p represents 0, 1 or 2.

The present invention also includes a method for controlling undesirable plant species comprising application of at least one compound of group (1) and at least one compound of group (2), as defined above. In the method of this invention, these compounds may be applied separately or together, in herbicidally effective amounts.

DETAILED DESCRIPTION OF THE PREFERRED EMBODIMENTS

Preferred embodiments of the composition and method of the present invention include those in which $A_1$ and/or $A_2$ are preferably phenyl, thienyl or pyrazol groups, independently substituted by one or more substituents selected from fluorine or chlorine atoms, or methyl, methoxy, trifluoromethyl or trifluoromethoxy groups.

Preferably, $R_1$ represents trifluoromethyl, methylthio or methyl and $R_2$ a hydrogen atom, or $R_1$ represents a hydrogen atom and $R_2$ is a hydrogen or chlorine atom.

Further preferred embodiments include those in which $A_3$ is suitably pyridyl or pyrazolyl, and $A_4$ pyridyl, pyrazolyl, phenyl or benzyl. $A_3$ and $A_4$ may be the same or different, and are preferably substituted, e.g. by halogen atoms, nitro, cyano, alkyl, alkoxy, alkylthio, aryl or haloalkyl groups wherein the alkyl moiety in each case preferably contains 1 to 6 carbon atoms.

Preferred compounds for use as 2,6-disubstituted pyridines according to the invention include the compounds of formulae III and IV:

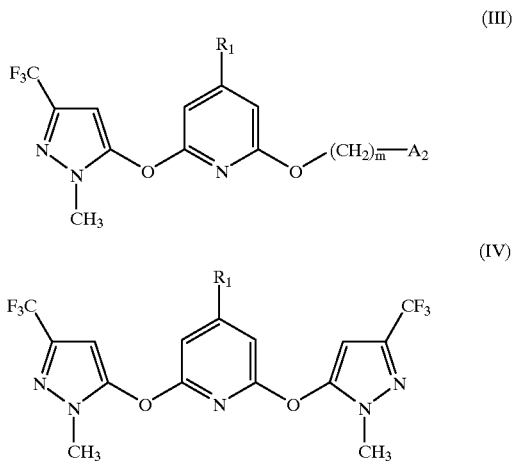

wherein $A_2$ represents an aryl, preferably a phenyl group which may be substituted by one or more of the same or different substituents selected from halogen atoms, $C_1$–$C_4$-alkyl, -alkoxy, -haloalkyl, -haloalkoxy groups, $R_1$ represents a hydrogen atom or a $C_1$–$C_4$-alkyl, -alkoxy, -alkylthio or -haloalkyl group, and m is 0, 1 or 2.

Particularly preferred are those compounds of formula III wherein $R_1$ is methyl, m is 1 and $A_2$ is phenyl or 4-fluorophenyl, and compounds of formula IV wherein $R_1$ is a hydrogen atom or a methyl group.

The pattern of persistence of the 2,6-substituted pyridine (abbreviated herein as "BAP") is such that the combined treatment according to the present invention can be attained either by the application of a prepared mixture as defined above, or by time separated application of separate formulations. Hence, in another preferred embodiment, the present invention provides a method for controlling the growth of weeds at a cereal crop locus which comprises applying to the locus a BAP as defined above and a second component which is selected from those listed above as group (1).

The treatment according to the invention may be used to control a broad spectrum of weed species in cereal crops, e.g., in wheat, barley, rice and maize, by pre- or post-emergence treatment, including both early and late post-emergence. The combined use decribed above offers both foliar and residual activity.

By the term "pre-emergence application" is meant application to the soil in which the weed seeds or seedlings are present before emergence of the weeds above the surface of the soil. By the term "post-emergence application" is meant application to the aerial or exposed portions of the weeds which have emerged above the surface of the soil. It will be appreciated that application according to the method may be from pre- to post-weed emergence, and from pre-crop emergence to post-crop emergence. By the term "foliar activity" is meant herbicidal activity obtained by application to the aerial or exposed portions of the weeds which have emerged above the surface of the soil. By the term "residual activity" is meant herbicidal activity obtained some time after application to the soil whereby seedlings present at the time of application or which germinate subsequent to application are controlled.

Weeds that may be controlled by the practice of the present invention include:

| | | |
|---|---|---|
| Veronica persica | Veronica hederaefolia | Stellaria media |
| Lamium purpureum | Lamium amplexicaule | Aphanes arvensis |
| Galium aparine | Alopecurus myosuroides | Matricaria inodora |
| Matricaria matricoides | Anthemis arvensis | Papaver rhoeas |
| Poa annua | Apera spica-venti | Phalaris paradoxa |
| Phalaris minor | Avena fatua | Lolium perenne |
| Bromus sterilis | Poa trivialis | Spergula arvensis |
| Cerastes holosteoides | Arenaria seryllifolia | Silene vulgaris |
| Legousia hybrida | Geranium dissectum | Montia perfoliata |
| Myosotis arvensis | Chenopodium alba | Polygonum aviculare |
| Polygonum lapathifolium | Polygonum convolvulus | Galeopsis tetrahit |
| Chrysantemum segetum | Centaurea cyanus | Viola arvensis |
| Senecia vulgaris | Cirsium arvense | Fumaria officinalis |
| Raphanus raphanistrum | Agrostis stolonifera | Atriplex patula |
| Capsella bursa-pastoris | Thlaspi arvense | Portulaca oleracea |
| Setaria viridis | Eleusine indica | Euphorbia helioscopia |

The application rate of the BAP component of this invention is usually in the range of 7.5 to 150 grams of active ingredient (g a.i.) per hectare, with rates between 7.5–100 g a.i./ha often achieving satisfactory control and selectivity. The optimal rate for a specific application will depend on the crop(s) under cultivation and the predominant species of infesting weed, and readily may be determined by established biological tests known to those skilled in the art.

The selection of the non-BAP active ingredient will likewise be dependent on the crop/weed situation to be treated, and will be readily identifiable by those skilled in this area. The application rate this active component is determined primarily by the chemical type of the component, since the intrinsic activity of different types of herbicide varies widely. For example, the activity of a triazine herbicide, such as cyanazine or simazine, can be almost tenfold greater than that of an urea herbicide such as chlortoluron or isoproturon. In general, the preferred application rate of this active ingredient is in the range of 100 to 2500 g a.i./ha, preferably 100–1500 g a.i./ha, for an urea herbicide; in the range of 7.5 to 100 g/ha, for a sulfonylurea herbicide; in the range of 75–400 g/ha for a hydroxybenzonitrile herbicide; in the range of 100–1200 g a.i./ha, for an aryloxyalkanoic acid herbicide; in the range of 250 to 2500 g/ha, for a dinitroaniline herbicide such as pendimethalin; in the range of 40 to 200 g/ha, for a pyridyloxyacetic acid herbicide such as fluroxypyr; in the range of 25 to 250 g/ha, for a fenoxyfenoxypropion acid herbicide; and in the range of 25 to 500 g/ha, for an oxyacetamide herbicide. The optimal rate for the chosen non-BAP component will, however, depend on the crop(s) under cultivation and the level of weed infestation, and can readily be determined by established biological tests. Naturally, with such a wide variation in application rate for the non-BAP component, the ratio of a BAP to a non-BAP component in the present invention will be determinded predominantly by the choice of the non-BAP component. Thus, the preferred ratio BAP:non-BAP may vary, e.g., from about 1:1 (Bromoxynil) to about 64:1 (Isoproturon).

The active compounds can be used in the form of a mixture of separate formulations, typically mixed with water prior to application (tank-mixtures), or as separate formulations applied individually within a certain time interval. Both active compounds can also be formulated together in a suitable ratio according to the present invention, together with usual carriers and/or additives known in the art.

A typical formulation containing one compound of group (1) and one compound of group (2) above may be composed as follows:

| Wettable Powder | |
|---|---|
| Compound C | 25 g |
| Isoproturon | 500 g |
| ligninsulfonate[1] | 80 g |
| alkylnaphthalene sulphonate[2] | 20 g |
| kaolin[3] | to 1000 g |

[1] e.g. Borresperse N (dispersing agent)
[2] e.g. Nekal BX (dispersing agent)
[3] e.g. China Clay GTY (filler/carrier)

Formulations of the present invention may be in any form known in the art, e.g., powders, granules, solutions, emulsions, suspensions, and the like.

The following examples illustrate specific embodiments of the present invention; however, the invention is not limited to the embodiments so illustrated, but includes the entire scope of the appended claims.

EXAMPLES

General Method:

The trials are carried out under greenhouse conditions in pre- and post-emergence applications. The plant seeds are sown in pots containing a loamy sand soil (0.5 l). The herbicides are applied as single treatments, or in a combination comprising a BAP compound and a non-BAP compound as designated, before or after emergence of weeds and crop. The herbicidal performance is assessed as percent damage in comparison to the untreated control plants. The assessment is done 21 days after the treatment. Wheat and barley are treated at the 34 leaf stage, the broad-leaf weeds at the 24 leaf stage and annual grasses at the 2–3 leaf stage.

For the BAP component, compounds A to D are employed:

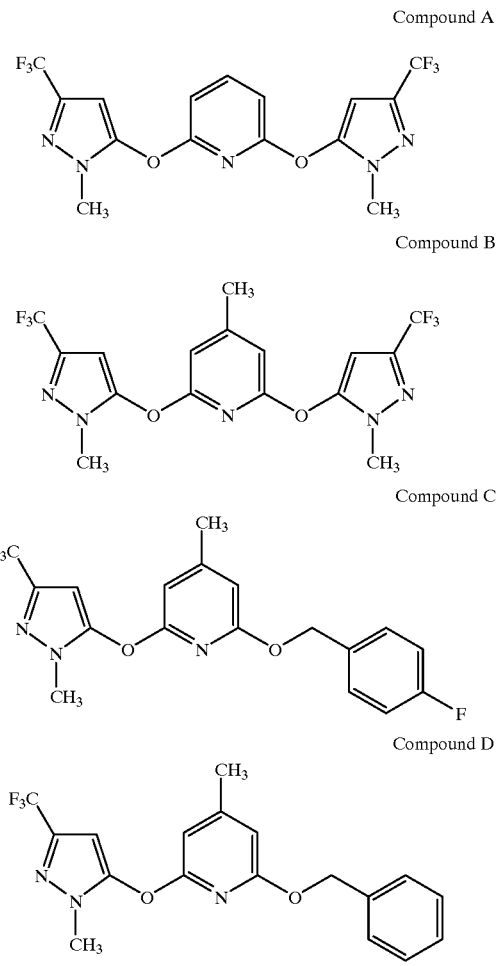

The non-BAP component is identified in each example with application rates (and hence component ratios) chosen to be appropriate to the established activity level of that component.

In the tables, "CCPP-P" means (R)-2-(4-chloro-2-methylphenoxy) proprionic acid.

The results of these experiments are tabulated as Examples 1 to 10, wherein all the results from a chosen "non-BAP component" are collected under the same Example number, different dosage rates/test species being recorded in the examples. From these results, it is clear that synergism exists between the BAP and the non-BAP compounds. Crop tolerance (wheat and barley) is excellent in all treatments.

Example 1a

Herbicidal performance of the mixture Compound A+loxynilsalt (30 g a.i./ha+60 g a.i./ha=mixture 1:2) against broad-leaved weeds in post-emergence application

| weed species | Compound A 30 g a.i./ha | Ioxynil 60 g a.i./ha | Compound A + Ioxynil 30 g a.i./ha + 60 g a.i./ha | |
|---|---|---|---|---|
| | % Control | | WE | W |
| Galium aparine (1.whorl) | 80 | 40 | 88 | 100 |
| Galium aparine (2.whorl) | 57 | 5 | 59 | 94 |
| Matricaria inodora | 1 | 89 | 89 | 100 |

WE = expected response by means of the Colby formula
W = observed response

Expected control of *Galium aparine* (1.whorl), *Galium aparine* (2.whorl) and *Matricaria inodora* was 88, 59 and 89%, resp., clearly demonstrating that the combination is synergistic.

Example 1b

Herbicidal performance of the mixture Compound A+Ioxynilsalt (15 g a.i./ha+60 g a.i./ha=mixture 1:4) against broad-leaved weeds in post-emergence application

| weed species | Compound A 15 g a.i./ha | Ioxynil 60 g a.i./ha | Compound A + Ioxynil 15 g a.i./ha + 60 g a.i./ha | |
|---|---|---|---|---|
| | % Control | | WE | W |
| Matricaria inodora | 1 | 89 | 89 | 100 |
| Papaver rhoeas | 79 | 0 | 79 | 97 |
| Myosotis arvensis | 72 | 37 | 82 | 100 |

WE = expected response by means of the Colby formula
W = observed response

Expected control of *Matricaria inodora, Papaver rhoes* and *Myosotis arvensis* was 89, 79 and 82% resp., clearly demonstrating that the combination is synergistic.

Example 1c

Herbicidal performance of the mixture Compound B+Ioxynilsalt (30 g a.i./ha+60 g a.i./ha=mixture 1:2) against broad-leaved weeds in post-emergence application

| weed species | Compound B 30 g a.i./ha | Ioxynil 60 g a.i./ha | Compound B + Ioxynil 30 g a.i./ha + 60 g a.i./ha | |
|---|---|---|---|---|
| | % Control | | WE | W |
| Galium aparine (1.whorl) | 83 | 40 | 90 | 100 |
| Galium aparine (2.whorl) | 67 | 5 | 69 | 85 |

WE = expected response by means of the Colby formula
W = observed response

Expected control of *Galium aparine* (1.whorl) and *Galium aparine* (2.whorl) was 90 and 69%, resp., clearly demonstrating that the combination is synergistic.

Example 1d

Herbicidal performance of the mixture Compound B+Ioxynilsalt (15 g a.i./ha+60 g a.i./ha=mixture 1:4) against broad-leaved weeds in post-emergence application

| weed species | Compound B 15 g a.i./ha | Ioxynil 60 g a.i./ha | Compound B + Ioxynil 15 g a.i./ha + 60 g a.i./ha | |
|---|---|---|---|---|
| | % Control | | WE | W |
| Galium aparine (1.whorl) | 80 | 40 | 88 | 100 |
| Galium aparine (2.whorl) | 60 | 5 | 62 | 82 |
| Matricaria inodora | 7 | 89 | 90 | 100 |

WE = expected response by means of the Colby formula
W = observed response

Expected control of *Galium aparine* (1.whorl), *Galium aparine* (2.whorl) and *Matricaria inodora* was 88, 62 and 90%, resp., clearly demonstrating that the combination is synergistic.

Example 2a

Herbicidal performance of the mixture Compound A+Bromoxynil Octanoate (60 g a.i./ha+60 g a.i./ha=mixture 1:1) against broad-leaved weeds in post-emergence application

| weed species | Compound A 60 g a.i./ha | Bromoxynil 60 g a.i./ha | Compound A + Bromoxynil 60 g a.i./ha + 60 g a.i./ha | |
|---|---|---|---|---|
| | % Control | | WE | W |
| Galium aparine (1.whorl) | 67 | 70 | 90 | 100 |
| Galium aparine (2.whorl) | 42 | 57 | 75 | 90 |
| Papaver rhoeas | 10 | 79 | 81 | 100 |

WE = expected response by means of the Colby formula
W = observed response

Expected control of *Galium aparine* (1.whorl), *Galium aparine* (2.whorl), *Stellaria media* and *Papaver rhoeas* was 90, 75 and 81%, resp., clearly demonstrating that the combination is synergistic.

Example 2b

Herbicidal performance of the mixture Compound A+Bromoxynil Octanoate (30 g a.i./ha+60 g a.i./ha=mixture 1:2) against broad-leaved weeds in post-emergence application

| weed species | Compound A 30 g a.i./ha | Bromoxynil 60 g a.i./ha | Compound A + Bromoxynil 30 g a.i./ha + 60 g a.i./ha | |
|---|---|---|---|---|
| | % Control | | WE | W |
| Galium aparine (1.whorl) | 57 | 70 | 87 | 92 |
| Galium aparine | 32 | 57 | 71 | 82 |

-continued

|  | Compound A 30 g a.i./ha | Bromoxynil 60 g a.i./ha | Compound A + Bromoxynil 30 g a.i./ha + 60 g a.i./ha | |
|---|---|---|---|---|
| weed species | % Control | | WE | W |
| (2.whorl) *Lamium purpureum* | 65 | 17 | 71 | 85 |
| *Stellaria media* | 45 | 0 | 45 | 69 |
| *Papaver rhoeas* | 9 | 79 | 81 | 100 |

WE = expected response by means of the Colby formula
W = observed response

Expected control of *Galium aparine* (1.whorl), *Galium aparine* (2.whorl), *Lamium purpureum*, *Stellaria media* and *Papaver rhoeas* was 87, 71, 71, 45 and 81%, resp., clearly demonstrating that the combination is synergistic.

Example 2c

Herbicidal performance of the mixture Compound A+Bromoxynil Octanoate (30 g a.i./ha+120 g a.i./ha= mixture 1:4) against broad-leaved weeds in post-emergence application

|  | Compound A 30 g a.i./ha | Bromoxynil 120 g a.i./ha | Compound A + Bromoxynil 30 g a.i./ha + 120 g a.i./ha | |
|---|---|---|---|---|
| weed species | % Control | | WE | W |
| *Galium aparine* (1.whorl) | 57 | 75 | 89 | 100 |
| *Galium aparine* (2.whorl) | 32 | 77 | 84 | 99 |
| *Stellaria media* | 65 | 57 | 85 | 90 |

WE = expected response by means of the Colby formula
W = observed response

Expected control of *Galium aparine* (1.whorl), *Galium aparine* (2.whorl) and *Stellaria media* was 89, 84 and 85%, resp., clearly demonstrating that the combination is synergistic.

Example 2d

Herbicidal performance of the mixture Compound B+Bromoxynil Octanoate (30 g a.i./ha+60 g a.i./ha=mixture 1:2) against broad-leaved weeds in post-emergence application

|  | Compound B 30 g a.i./ha | Bromoxynil 60 g a.i./ha | Compound B + Bromoxynil 30 g a.i./ha + 60 g a.i./ha | |
|---|---|---|---|---|
| weed species | % Control | | WE | W |
| *Galium aparine* (2.whorl) | 65 | 57 | 85 | 100 |
| *Stellaria media* | 62 | 0 | 62 | 84 |
| *Papaver rhoeas* | 17 | 79 | 83 | 100 |

WE = expected response by means of the Colby formula
W = observed response

Expected control of *Galium aparine* (2.whorl), *Stellaria media* and *Papaver rhoeas* was 85, 62 and 83%, resp., clearly demonstrating that the combination is synergistic.

Example 2e

Herbicidal performance of the mixture Compound B+Bromoxynil Octanoate (15 g a.i./ha+60 g a.i./ha=mixture 1:4) against broad-leaved weeds in post-emergence application

|  | Compound B 15 g a.i./ha | Bromoxynil 60 g a.i./ha | Compound B + Bromoxynil 15 g a.i./ha + 60 g a.i./ha | |
|---|---|---|---|---|
| weed species | % Control | | WE | W |
| *Galium aparine* (1.whorl) | 67 | 70 | 90 | 100 |
| *Stellaria media* | 47 | 0 | 47 | 83 |
| *Papaver rhoeas* | 2 | 79 | 79 | 100 |

WE = expected response by means of the Colby formula
W = observed response

Expected control of *Galium aparine* (1.whorl), *Stellaria media* and *Papaver rhoeas* was 90, 47 and 79%, resp., clearly demonstrating that the combination is synergistic.

Example 2f

Herbicidal performance of the mixture Compound B+Bromoxynil Octanoate (15 g a.i./ha+120 g a.i./ha= mixture 1:8) against broad-leaved weeds in post-emergence application

|  | Compound B 15 g a.i./ha | Bromoxynil 120 g a.i./ha | Compound B + Bromoxynil 15 g a.i./ha + 120 g a.i./ha | |
|---|---|---|---|---|
| weed species | % Control | | WE | W |
| *Galium aparine* (1.whorl) | 67 | 75 | 92 | 100 |
| *Galium aparine* (2.whorl) | 45 | 77 | 87 | 98 |
| *Stellaria media* | 47 | 0 | 47 | 75 |

WE = expected response by means of the Colby formula
W = observed response

Expected control of *Galium aparine* (1.whorl), *Galium aparine* (2.whorl) and *Stellaria media* was 92, 87 and 47%, resp., clearly demonstrating that the combination is synergistic.

Example 3a

Herbicidal performance of the mixture Compound A+CMPP-P (30 g a.i./ha+480 g a.i./ha=mixture 1:16) against broad-leaved weeds in post-emergence application

|  | Compound A 30 g a.i./ha | CMPP-P 480 g a.i./ha | Compound A + CMPP-P 30 g a.i./ha + 480 g a.i./ha | |
|---|---|---|---|---|
| weed species | % Control | | WE | W |
| *Papaver rhoeas* | 32 | 47 | 64 | 87 |
| *Lamium purpureum* | 62 | 67 | 87 | 99 |
| *Polygonum convolvulus* | 60 | 40 | 76 | 99 |

WE = expected response by means of the Colby formula
W = observed response

Expected control of *Papaver rhoeas, Lamium purpureum* and *Polygonum convolvulus* was 64, 87 and 76%, resp., clearly demonstrating that the combination is synergistic.

Example 4a
Herbicidal performance of the mixture Compound A+Amidosulfuron (50 g a.i./ha+15 g a.i./ha=mixture 3.3:1) against broad-leaved weeds in post-emergence application

| weed species | Compound A 50 g a.i./ha | Amidosulfuron 15 g a.i./ha | Compound A + Amidosulfuron 50 g a.i./ha + 15 g a.i./ha | |
|---|---|---|---|---|
| | % Control | | WE | W |
| Galium aparine (1.whorl) | 50 | 40 | 70 | 82 |
| Galium aparine (2.whorl) | 30 | 20 | 44 | 97 |

WE = expected response by means of the Colby formula
W = observed response

Expected control of *Galium aparine* (1.whorl) and *Galium aparine* (2.whorl) was 70 and 44%, resp., clearly demonstrating that the combination is synergistic.

Example 4b
Herbicidal performance of the mixture Compound B+Amidosulfuron (7.5 g a.i./ha+30 g a.i./ha=mixture 1:4) against broad-leaved weeds in post-emergence application

| weed species | Compound B 7.5 g a.i./ha | Amidosulfuron 30 g a.i./ha | Compound B + Amidosulfuron 7.5 g a.i./ha + 30 g a.i./ha | |
|---|---|---|---|---|
| | % Control | | WE | W |
| Veronica persica | 65 | 0 | 65 | 96 |
| Stellaria media | 25 | 50 | 63 | 87 |
| Papaver rhoeas | 7 | 15 | 21 | 65 |
| Lamium purpureum | 70 | 0 | 70 | 96 |

WE = expected response by means of the Colby formula
W = observed response

Expected control of *Veronica persica, Stellaria media, Papaver rhoeas* and *Lamium purpureum* was 65, 63, 21 and 70%, resp., clearly demonstrating that the combination is synergistic.

Example 5a
Herbicidal performance of the mixture Compound B+Fluroxypyr (30 g a.i./ha+90 g a.i./ha=mixture 1:3) against broad-leaved weeds in post-emergence application

| weed species | Compound B 30 g a.i./ha | Fluroxypyr 90 g a.i./ha | Compound B + Fluroxypyr 30 g a.i./ha + 90 g a.i./ha | |
|---|---|---|---|---|
| | % Control | | WE | W |
| Matricaria inodora | 22 | 45 | 57 | 95 |
| Papaver rhoeas | 80 | 0 | 80 | 92 |
| Polygonum convolvulus | 15 | 45 | 53 | 80 |

WE = expected response by means of the Colby formula
W = observed response

Expected control of *Matricaria inodora, Papaver rhoeas* and *Polygonum convolvulus* was 57, 80 and 53%, resp., clearly demonstrating that the combination is synergistic.

Example 5b
Herbicidal performance of the mixture Compound B+Fluroxypyr (15 g a.i./ha+120 g a.i./ha=mixture 1:8) against broad-leaved weeds in post-emergence application

| weed species | Compound B 15 g a.i./ha | Fluroxypyr 120 g a.i./ha | Compound B + Fluroxypyr 15 g a.i./ha + 120 g a.i./ha | |
|---|---|---|---|---|
| | % Control | | WE | W |
| Stellaria media | 45 | 67 | 82 | 100 |
| Veronica persica | 77 | 52 | 89 | 97 |
| Polygonum lapathifolium | 17 | 80 | 83 | 98 |

WE = expected response by means of the Colby formula
W = observed response

Expected control of *Stellaria media, Veronica persica* and *Polygonum lapathifolium* was 82, 89 and 83%, resp., clearly demonstrating that the combination is synergistic.

Example 6a
Herbicidal performance of the mixture Compound B+Cyanazine (30 g a.i./ha+120 g a.i./ha=mixture 1:4) against broad-leaved weeds in post-emergence application

| weed species | Compound B 30 g a.i./ha | Cyanazine 120 g a.i./ha | Compound B + Cyanazine 30 g a.i./ha + 120 g a.i./ha | |
|---|---|---|---|---|
| | % Control | | WE | W |
| Galium aparine (1.whorl) | 52 | 5 | 54 | 86 |
| Galium aparine (2.whorl) | 45 | 0 | 45 | 72 |
| Galium aparine (3.whorl) | 40 | 0 | 40 | 75 |
| Stellaria media | 42 | 61 | 77 | 100 |
| Matricaria inodora | 22 | 52 | 63 | 100 |
| Papaver rhoeas | 80 | 0 | 86 | 100 |
| Polygonum convolvulus | 7 | 60 | 63 | 100 |

WE = expected response by means of the Colby formula
W = observed response

Expected control of *Galium aparine* (1.whorl), *Galium aparine* (2.whorl), *Galium aparine* (3.whorl), *Stellaria media, Matricaria inodora, Papaver rhoeas* and *Polygonum convolvulus* was 54, 45, 40, 77, 63, 80 and 63%, resp., clearly demonstrating that the combination is synergistic.

Example 6b
Herbicidal performance of the mixture Compound B+Cyanazine (15 g a.i./ha+120 g a.i./ha=mixture 1:8) against broad-leaved weeds in post-emergence application

|  | Compound B 15 g a.i./ha | Cyanazine 120 g a.i./ha | Compound B + Cyanazine 15 g a.i./ha + 120 g a.i./ha | |
| --- | --- | --- | --- | --- |
| weed species | % Control | | WE | W |
| Stellaria media | 27 | 61 | 72 | 100 |
| Matricaria inodora | 20 | 52 | 62 | 100 |
| Polygonum convolvulus | 7 | 60 | 63 | 97 |

WE = expected response by means of the Colby formula
W = observed response

Expected control of *Stellaria media, Matricaria inodora* and *Polygonum convolvulus* was 72, 62 and 63%, resp., clearly demonstrated that the combination is synergstic.

Example 6c

Herbicidal performance of the mixture Compound B+Cyanazine (30 g a.i./ha+240 g a.i./ha=mixture 1:8) against broad-leaved weeds in post-emergence application

|  | Compound B 30 g a.i./ha | Cyanazine 240 g a.i./ha | Compound B + Cyanazine 30 g a.i./ha + 240 g a.i./ha | |
| --- | --- | --- | --- | --- |
| weed species | % Control | | WE | W |
| Galium aparine (1.whorl) | 52 | 10 | 57 | 92 |
| Galium aparine (2.whorl) | 45 | 10 | 51 | 95 |
| Galium aparine (3.whorl) | 40 | 5 | 43 | 81 |
| Stellaria media | 42 | 72 | 84 | 100 |
| Matricaria inodora | 22 | 85 | 88 | 100 |
| Papaver rhoeas | 80 | 0 | 80 | 100 |

WE = expected response by means of the Colby formula
W = observed response

Expected control of *Galium aparine* (1.whorl), *Galium aparine* (2.whorl), *Galium aparine* (3.whorl), *Stellaria media, Matricaria inodora* and *Papaver rhoeas* was 57, 51, 43, 84, 88 and 80%, resp., clearly demonstrating that the combination is synergistic.

Example 6d

Herbicidal performance of the mixture Compound B+Cyanazine (15 g a.i./ha+240 g a.i./ha=mixture 1:16) against broad-leaved weeds in post-emergence application

|  | Compound B 15 g a.i./ha | Cyanazine 240 g a.i./ha | Compound B + Cyanazine 15 g a.i./ha + 240 g a.i./ha | |
| --- | --- | --- | --- | --- |
| weed species | % Control | | WE | W |
| Galium aparine (1.whorl) | 40 | 10 | 46 | 85 |
| Galium aparine (2.whorl) | 37 | 10 | 43 | 77 |
| Galium aparine (3.whorl) | 40 | 5 | 43 | 60 |
| Stellaria media | 27 | 72 | 80 | 100 |
| Matricaria inodora | 20 | 85 | 88 | 100 |
| Papaver rhoeas | 60 | 0 | 60 | 87 |

WE = expected response by means of the Colby formula
W = observed response

Expected control of *Galium aparine* (1.whorl), *Galium aparine* (2.whorl), *Galium aparine* (3.whorl), *Stellaria media, Matricaria inodora* and *Papaver rhoeas* was 46, 43, 43, 80, 88 and 60%, resp., clearly demonstrating that the combination is synergistic.

Example 7a

Herbicidal performance of the mixture Compound C+Isoproturon (50 g a.i./ha+150 g a.i./ha=mixture 1:3) against grasses in post-emergence application

|  | Compound C 50 g a.i./ha | Isoproturon 150 g a.i./ha | Compound C + Isoproturon 50 g a.i./ha + 150 g a.i./ha | |
| --- | --- | --- | --- | --- |
| grass | % control | | WE | W |
| Alopecurus myosuroides | 88 | 30 | 91 | 100 |
| Setaria viridis | 75 | 58 | 89 | 100 |
| Lolium perenne | 78 | 10 | 80 | 100 |

WE = expected response by means of the Colby formula
W = observed response

Expected control of *Alopecurus myosuroides, Setaria viridis* and *Lolium perenne* was 91, 89 and 80%, resp., clearly demonstrated that the combination is synergistic.

Example 7b

Herbicidal performance of the mixture Compound C+Isoproturon (25 g a.i./ha+150 g a.i./ha=mixture 1:6) against grasses in post-emergence application

|  | Compound C 25 g a.i./ha | Isoproturon 150 g a.i./ha | Compound C + Isoproturon 25 g a.i./ha + 150 g a.i./ha | |
| --- | --- | --- | --- | --- |
| grass | % control | | WE | W |
| Alopecurus myosuroides | 83 | 30 | 88 | 100 |
| Setaria viridis | 55 | 58 | 81 | 100 |
| Lolium perenne | 65 | 10 | 69 | 94 |

WE = expected response by means of the Colby formula
W = observed response

Expected control of *Alopecurus myosuroides, Setaria viridis* and *Lolium perenne* was 88, 81 and 69%, resp., clearly demonstrating that the combination is synergistic.

Example 7c

Herbicidal performance of the mixture Compound C+Isoproturon (12.5 g a.i./ha+150 g a.i./ha=mixture 1:12) against grasses in post-emergence application

| grass | Compound C 12.5 g a.i./ha | Isoproturon 150 g a.i./ha | Compound C + Isoproturon 12.5 g a.i./ha + 150 g a.i./ha | |
|---|---|---|---|---|
| | % control | | WE | W |
| Alopecurus myosuroides | 65 | 30 | 76 | 88 |
| Setaria viridis | 30 | 58 | 70 | 94 |
| Lolium perenne | 38 | 10 | 44 | 91 |
| Poa annua | 75 | 65 | 91 | 99 |

WE = expected response by means of the Colby formula
W = observed response

Expected control of *Alopecurus myosuroides, Setaria viridis, Lolium perenne* and *Poa annua* was 76, 70, 44 and 91%, resp., clearly demonstrating that the combination is synergistic.

Example 7d

Herbicidal performance of the mixture Compound C+Isoproturon (25 g a.i./ha+300 g a.i./ha=mixture 1:12) against grasses in post-emergence application

| grass | Compound C 25 g a.i./ha | Isoproturon 300 g a.i./ha | Compound C + Isoproturon 25 g a.i./ha + 300 g a.i./ha | |
|---|---|---|---|---|
| | % control | | WE | W |
| Alopecurus myosuroides | 83 | 73 | 95 | 100 |
| Lolium perenne | 65 | 40 | 79 | 98 |

WE = expected response by means of the Colby formula
W = observed response

Expected control of *Alopecurus mysuroides* and *Lolium perenne* was 95 and 79%, reps., clearly demonstrated that he combination is synergistic.

Example 7e

Herbicidal performance of the mixture Compound C+Isoproturon (12.5 g a.i./ha+300 g a.i./ha=mixture 1:24) against grasses in post-emergence application

| grass | Compound C 12.5 g a.i./ha | Isoproturon 300 g a.i./ha | Compound C + Isoproturon 12.5 g a.i./ha + 300 g a.i./ha | |
|---|---|---|---|---|
| | % control | | WE | W |
| Alopecurus myosuroides | 65 | 73 | 90 | 99 |
| Lolium perenne | 38 | 40 | 63 | 91 |
| Poa annua | 75 | 83 | 96 | 100 |

WE = expected response by means of the Colby formula
W = observed response

Expected control of *Alopecurus myosuroides, Lolium perenne* and *Poa annua* was 90, 63 and 96%, resp., clearly demonstrating that the combination is synergistic.

Example 7f

Herbicidal performance of the mixture Compound A+Isoproturon (30 g a.i./ha+1920 g a.i./ha=mixture 1:64) against broad-leaved weeds in post-emergence application

| weed species | Compound A 30 g a.i./ha | Isoproturon 1920 g a.i./ha | Compound A + Isoproturon 30 g a.i./ha + 1920 g a.i./ha | |
|---|---|---|---|---|
| | % Control | | WE | W |
| Veronica persica | 81 | 0 | 81 | 97 |
| Lamium purpureum | 35 | 3 | 37 | 97 |
| Myosotis arvensis | 57 | 25 | 68 | 99 |
| Viola arvensis | 75 | 65 | 91 | 100 |
| Polygonum convolvulus | 5 | 4 | 9 | 80 |
| Galium aparine (2.whorl) | 75 | 0 | 75 | 90 |

WE = expected response by means of the Colby formula
W = observed response

Expected control of *Veronica persica, Lamium purpureum, Myosotis arvensis, Viola arvensis, Polygonum convolvulus* and *Galium aparine* (2.whorl) was 81, 37, 68, 91, 9 and 75% resp., clearly demonstrating that the combination is synergistic.

Example 7g

Herbicidal performance of the mixture Compound D+Isoproturon (15 g a.i./ha+300 g a.i./ha=mixture 1:20) against *Alopecurus myosuroides* in pre-emergence application

| weed species | Compound D 15 g a.i./ha | Isoproturon 120 g a.i./ha | Compound D + Isoproturon 15 g a.i./ha + 120g a.i./ha | |
|---|---|---|---|---|
| | % Control | | WE | W |
| Alopecurus myosuroides | 60 | 75 | 90 | 99 |

WE = expected response by means of the Colby formula
W = observed response

Expected control of *Alopecurus myosuroides* was 90%, resp., clearly demonstrating that the combination is synergistic.

Example 8a

Herbicidal performance of the mixture Compound D+Pendimethalin (15 g a.i./ha+450 g a.i./ha=mixture 1:30) against *Alopecurus myosuroides* in pre-emergence application

| | Compound D 15 g a.i./ha | Pendimethalin 450 g a.i./ha | Compound D + Pendimethalin 15 g a.i./ha + 450 g a.i./ha | |
|---|---|---|---|---|
| weed species | % Control | | WE | W |
| Alopecurus myosuroides | 57 | 35 | 72 | 90 |

WE = expected response by means of the Colby formula
W = observed response

Expected control of *Alopecurus myosuroides* was 72%, resp., clearly demonstrating that the combination is synergistic.

Example 8b

Herbicidal performance of the mixture Compound D+Pendimethalin (15 g a.i./ha+900 g a.i./ha=mixture 1:60) against *Alopecurus myosuroides* in pre-emergence application

| | Compound D 15 g a.i./ha | Pendimethalin 900 g a.i./ha | Compound D + Pendimethalin 15 g a.i./ha + 900 g a.i./ha | |
|---|---|---|---|---|
| weed species | % Control | | WE | W |
| Alopecurus myosuroides | 57 | 55 | 81 | 96 |

WE = expected response by means of the Colby formula
W = observed response

Expected control of *Alopecurus myosuroides* was 81%, resp., clearly demonstrating that the combination is synergistic Example 9a Herbicidal performance of the mixture Compound C+Fenoxaprop (12.5 g a.i./ha+15 g a.i./ha=mixture 1:1,2) against *Setaria viridis* in post-emergence application

| | Compound C 12.5 g | Fenoxaprop 15 g a.i./ha | Compound C + Fenoxaprop 12.5 g a.i./ha + 15 g a.i./ha | |
|---|---|---|---|---|
| weed species | % Control | | WE | W |
| Setaria viridis | 30 | 62 | 73 | 94 |

WE = expected response by means of the Colby formula
W = observed response

Expected control of *Setaria viridis* was 73%, resp., clearly demonstrating that the combination is synergistic.

Example 9b

Herbicidal performance of the mixture Compound C+Fenoxaprop (12.5 g a.i./ha+30 g a.i./ha=mixture 1:2.4) against *Setaria viridis* in post-emergence application

| | Compound C 12.5 g a.i./ha | Fenoxaprop 30 g a.i./ha | Compound C + Fenoxaprop 12.5 g a.i./ha + 30 g a.i./ha | |
|---|---|---|---|---|
| weed species | % Control | | WE | W |
| Setaria viridis | 30 | 72 | 80 | 93 |

WE = expected response by means of the Colby formula
W = observed response

Expected control of *Setaria viridis* was 80%, resp., clearly demonstrating that the combination is synergistic.

Example 9c

Herbicidal performance of the mixture Compound C+Fenoxaprop (12.5 g a.i./ha+60 g a.i./ha=mixture 1:4.8) against *Setaria viridis* in post-emergence application

| | Compound C 12.5 g a.i./ha | Fenoxaprop 60 g a.i./ha | Compound C + Fenoxaprop 12.5 g a.i./ha + 60 g a.i./ha | |
|---|---|---|---|---|
| weed species | % Control | | WE | W |
| Setaria viridis | 30 | 77 | 84 | 100 |

WE = expected response by means of the Colby formula
W = observed response

Expected control of *Setaria viridis* was 84%, resp., clearly demonstrating that the combination is synergistic.

I claim:

1. A herbicidal composition comprising a herbicidally acceptable carrier and/or surface active agent and, as active ingredient, synergistic herbicidal effective amount of the mixture of (1) about 7.5 to 150 parts by weight of at least one 2,6-disubstituted pyridine of formula III

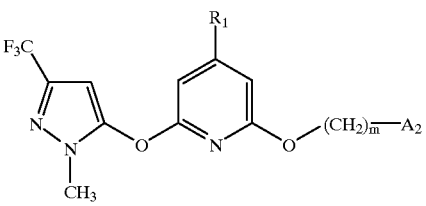

(III)

wherein $A_2$ represents an aryl group which may be substituted by one or more of the same or different substituents selected from halogen atoms, $C_1$–$C_4$-alkyl, -alkoxy, -haloalkyl, and -haloalkoxy groups, $R_1$ represents a hydrogen atom or a $C_1$–$C_4$-alkyl, -alkoxy, -alkylthio or -haloalkyl group, and m is 0 or 1; and (2) about 100 to 2500 parts by weight of at least one additional herbicidal compound selected from the group consisting of chlortoluron, isoproturon, linuron, neburon, atrazine, cyanazine, simazine, bromoxynil, ioxynil, dichloroprop, MCPA, mecoprop, pendimethalin, amidosulfuron, pyridate, flurenol, fluroxypyr, and fenoxaprop.

2. A herbicidal composition according to claim 1 wherein the 2,6-disubstituted pyridine is a compound of formula C or D Compound C

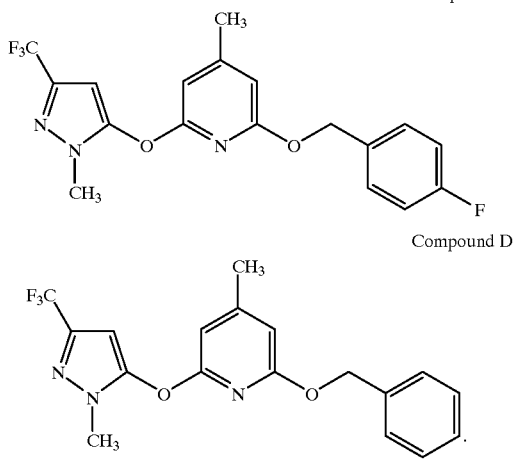

Compound D

3. A composition as claimed in claim 2 comprising Compound D and pendimethalin.

4. A method of controlling the growth of weeds at a locus which comprises applying to the locus a synergistic herbicidally effective amount of both a compound of group (1) and a compound of group (2) as defined in claim 1.

5. The method according to claim 4, wherein said compounds are applied together in a single formulation.

6. The method according to claim 4, wherein said compounds are applied in separate formulations.

7. The method according to claim 4 wherein about 7.5 to 150 grams of a compound of group (1) and about 100 to 2500 grams of a compound of group (2) are applied.

8. The method according to claim 4 wherein about 7.5 to 100 grams of a compound of group (1) and about 250 to 2500 grams of a compound of group (2) are applied.

9. A method for controlling the growth of weeds in cereal crops comprising applying thereto a synergistic herbicidally effective amount of a composition according to claim 1.

10. A method for controlling the growth of weeds in cereal crops comprising applying thereto a synergistic herbicidally effective amount of a composition according to claim 1.

11. A method for controlling the growth of weeds in cereal crops comprising applying thereto a synergistic herbicidally effective amount of a composition according to claim 1.

12. A method of controlling the growth of weeds at a locus, which comprises applying to the locus synergistic herbicidally effective amounts of:

a) from about 7.5 to about 150 grams per hectare of a 2,6-disubstituted pyridine of formula III

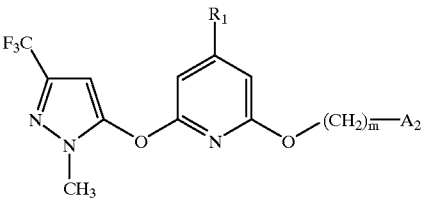

(III)

wherein $A_2$ represents an aryl group which may be substituted by one or more of the same or different substituents selected from halogen atoms, $C_1$–$C_4$-alkyl, -alkoxy, -haloalkyl, and -haloalkoxy groups, $R_1$ represents a hydrogen atom or a $C_1$–$C_4$-alkyl, -alkoxy, -alkylthio or -haloalkyl group, and m is 1; and b) from about 100 to 2500 grams per hectare of at least one second herbicidal compound selected from the group consisting of chlortoluron, isoproturon, linuron, neburon, atrazine, cyanazine, simazine, bromoxynil, ioxynil, dichloroprop, MCPA, mecoprop, pendimethalin, amidosulfuron, pyridate, flurenol, fluroxypyr, and fenoxaprop.

* * * * *